US00PP31235P2

(12) United States Plant Patent
Zlesak

(10) Patent No.: US PP31,235 P2
(45) Date of Patent: Dec. 17, 2019

(54) ***PHYSOCARPUS* PLANT NAMED 'ZLEBIC5'**

(50) Latin Name: *Physocarpus opulifolius*
Varietal Denomination: ZLEBic5

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 97 days.

(21) Appl. No.: 15/732,781

(22) Filed: Dec. 29, 2017

(51) Int. Cl.
*A01H 5/02* (2018.01)

(52) U.S. Cl.
USPC ..... Plt./226

(58) Field of Classification Search
USPC ..... Plt./226
CPC ..... A01H 5/02
See application file for complete search history.

(56) References Cited

PUBLICATIONS

Plant Nouveau Catalog, Jul. 9, 2017, p. 55.*

* cited by examiner

*Primary Examiner* — Keith O. Robinson

(57) ABSTRACT

'ZLEBic5' is a new and distinct cultivar of *Physocarpus opulifolius* plant having an upright, mounded, dense plant habit; compact overall plant size; strong branching characteristics; small orange-red foliage as it emerges that matures to purple; short internode length; resistance to powdery mildew; corymbs of small pink-white flowers that are produced in late spring into early summer and again on current season terminal growth later in summer and into fall; coral pink to red follicle color in full sun for about a month after fertilization; and ability to root and grow vigorously from softwood and semi-hardwood stem cuttings.

7 Drawing Sheets

Latin name of the plant claimed: *Physocarpus opulifolius*.
Variety denomination: 'ZLEBic5'.

BACKGROUND OF THE INVENTION

The present invention relates to a new and distinct cultivar of *Physocarpus opulifolius* and will be referred to hereafter by its cultivar name, 'ZLEBic5'. *Physocarpus opulifolius* is a deciduous shrub grown for landscape use. The key objective within the *Physocarpus opulifolius* breeding program I initiated in St. Paul, Minn. was to develop new *Physocarpus opulifolius* cultivars that are compact growing, well-branched, healthy, and possess colorful foliage. One objective has been to produce a cultivar with the orange-red new foliage color which matures to purple of *Physocarpus opulifolius* 'Center Glow' (disclosed in U.S. Plant Pat. No. 16,894) and the compact, well-branched growth habit and small foliage of cultivated ninebark such as *Physocarpus opulifolius* as var. *nanus* (not patented) or its descendant *Physocarpus opulifolius* 'Donna May' (disclosed in U.S. Plant Pat. No. 22,634).

'ZLEBic5' originated by crossing *Physocarpus opulifolius* 'Donna May' as the female parent and *Physocarpus opulifolius* 'Dart's Gold' (not patented) as the male parent. The pollination that led to the population of seedlings from which 'ZLEBic5' was identified occurred in June 2011. The seeds of this population germinated during the winter of 2011/2012 indoors under florescent lights in St. Paul, Minn. Seedlings were grown in containers during their first year. At the end of the first growing season, seedlings with attractive foliage color, relatively compact growth habits, and powdery mildew resistance were retained. Selections were planted outside during their second growing season.

'ZLEBic5' was recognized as a highly desirable genotype among this seedling population during the summer of 2012. 'ZLEBic5' was planted outside in 2013 and was first asexually propagated using semi-hardwood stem cuttings in the spring of 2013. I have found that the characteristics of 'ZLEBic5' are stable and true to type over successive generations of vegetative propagation.

'ZLEBic5' was unique from other ninebark seedlings in the breeding program because of its warm orange to red new growth that matured to purple foliage and stems and compact, very well-branched plant habit. 'ZLEBic5' first flowered in 2014. It has attractive pink-white flowers that are abundant and attractive against the colorful foliage. As follicles develop, they are a coral pink to red color for about a month and provide additional ornamental value. 'ZLEBic5' displays the very unique trait in ninebark of reliable repeat flowering. Under favorable growing conditions stems from mid-summer until fall can terminate with a corymb of flowers. Repeat flowering during the same growing season leads to a very nicely branched plant as multiple axillary buds under corymbs typically begin growing, which can lead to stems that also terminate in flowers the same growing season. Since the new growth has an attractive warm orange-red color before darkening to purple, reblooming and abundant natural branching without pruning results in many colorful growing points and a dense plant.

SUMMARY OF THE INVENTION

The primary objective of the breeding project was substantially achieved, along with other desirable improvements, as evidenced by the following unique combination of characteristics that are outstanding in the new variety and that distinguish it from its parents, as well as from all other varieties of *Physocarpus opulifolius* of which I am aware:

1. Upright, mounded, dense plant habit;
2. Compact overall plant size;
3. Strong branching characteristics;
4. Small orange-red foliage as it emerges that matures to purple;
5. Short internode length;
6. Resistance to powdery mildew;
7. Corymbs of small pink-white flowers that are produced in late spring into early summer and again on current season terminal growth later in summer and into fall;
8. Coral pink to red follicle color in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls and Menomonie Falls, Wis. and St. Paul, Minn. shows that the foregoing and all other characteristics and distinctions come true to form and are established and transmitted through succeeding asexual propagations.

COMPARISON WITH PARENTS

'ZLEBic5' has similar foliage size, mature plant size, flower size, flower color, and fruit size as its female parent, 'Donna May'. 'ZLEBic5' differs from 'Donna May' in that new growth of 'ZLEBic5' has a warm orange-red color before it matures to purple versus 'Donna May' having purple or greenish-purple new growth before it matures to purple. 'ZLEBic5' reliably reblooms later in the growing season on terminals of vigorous new stems. 'Donna May' can rebloom later in the growing season, but does so much less reliably and abundantly. The reliable and more abundant rebloom of 'ZLEBic5' than 'Donna May' at stem terminals leads to greater branching in 'ZLEBic5' and results in a more dense and full plant habit.

'ZLEBic5' differs in a number of ways from its male parent 'Dart's Gold'. 'ZLEBic5' has smaller leaves, smaller flowers, smaller fruit, shorter internodes, and an overall smaller plant size than 'Dart's Gold'. The foliage of 'ZLEBic5' is a warm orange-red color maturing to purple, whereas the foliage color of 'Dart's Gold' is yellow-green. The flowers of 'ZLEBic5' have more pink in them and follicles are more richly pigmented with red during development than 'Dart's Gold'. 'ZLEBic5' reliably reblooms later in the growing season and I have not observed rebloom on 'Dart's Gold'. 'ZLEBic5' branches much more freely and has a more dense plant habit than 'Dart's Gold'. The greatest similarity between 'ZLEBic5' and 'Dart's Gold' is that both have warm colored new growth ('ZLEBic5' has orange-red new growth and 'Dart's Gold' has yellow-green new growth).

COMPARISON OF 'ZLEBIC5' WITH SIMILAR CULTIVAR

The *Physocarpus opulifolius* cultivar that shares similarity in foliage color with 'ZLEBic5' is 'Center Glow' (disclosed in U.S. Plant Pat. No. 16,894). New growth is a warm orange-red color maturing to purple. 'ZLEBic5' has smaller leaves, smaller flowers, a smaller mature plant size, and more abundant branching than 'Center Glow'. 'ZLEBic5' reliably reblooms in mid-summer and into fall, while 'Center Glow' does not reliably rebloom.

BRIEF DESCRIPTION OF THE DRAWINGS

The accompanying colored photographs illustrate the overall appearance of 'ZLEBic5'. Photographs show the colors as true as it is reasonably possible to obtain with colored reproductions of this type. Colors in the photographs may differ slightly from the color values cited in the detailed botanical description, which accurately describe the colors of 'ZLEBic5'.

DETAILED BOTANICAL DESCRIPTION

Figure 1:
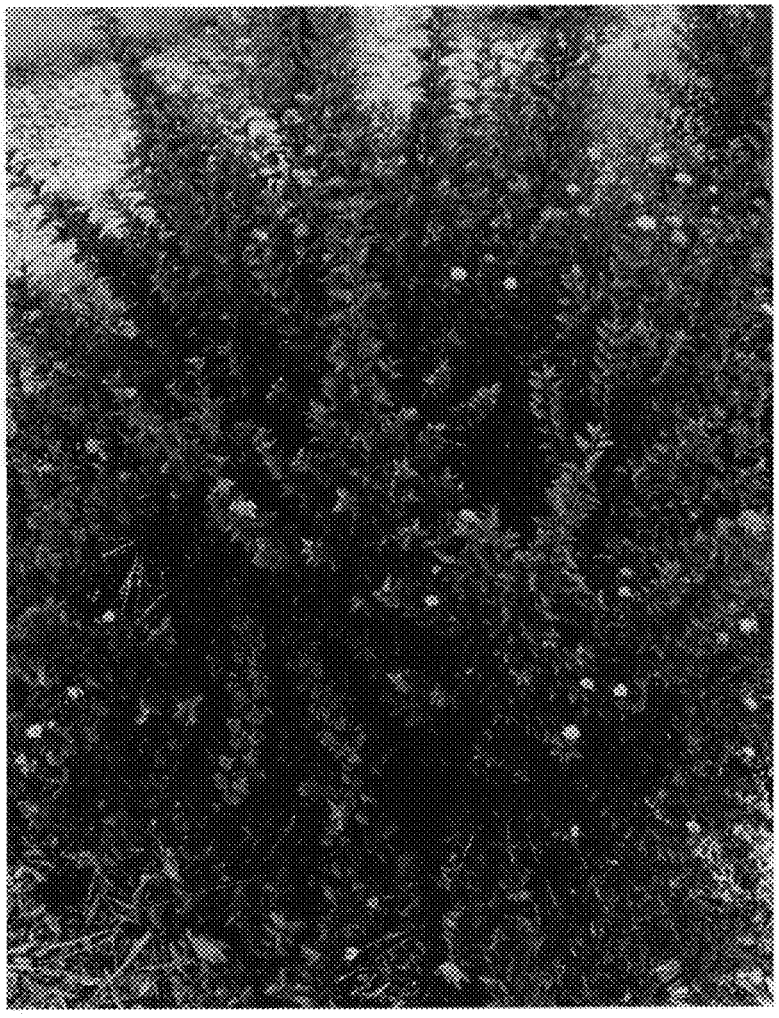
FIG. 1 illustrates a four-year-old plant of 'ZLEBic5' displaying rebloom on terminals of current season branches August 2016.
Figure 2:
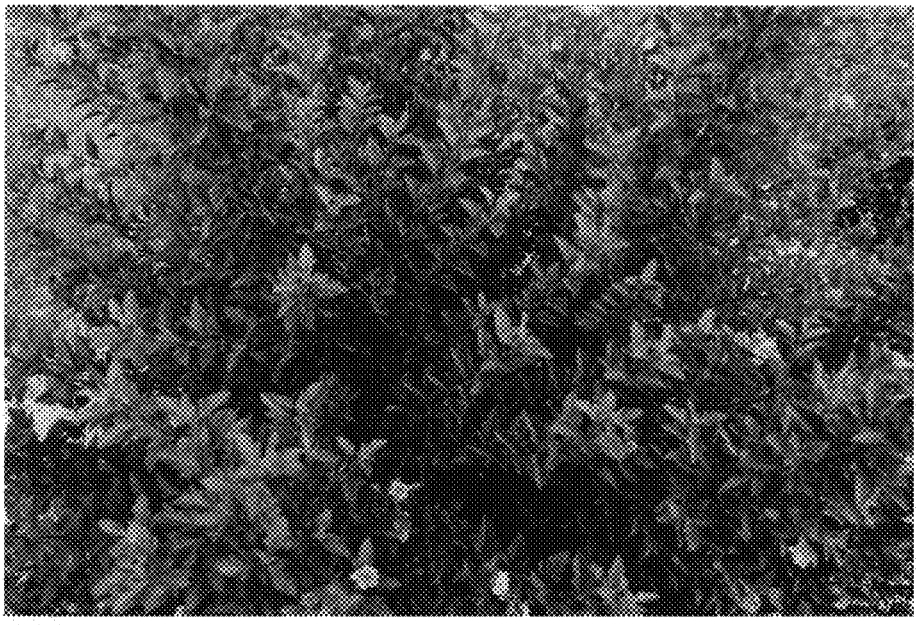
FIG. 2 illustrates abundant branching of 'ZLEBic5' on current season stems without pruning and warm orange-red emerging foliage August 2016.
Figure 3:
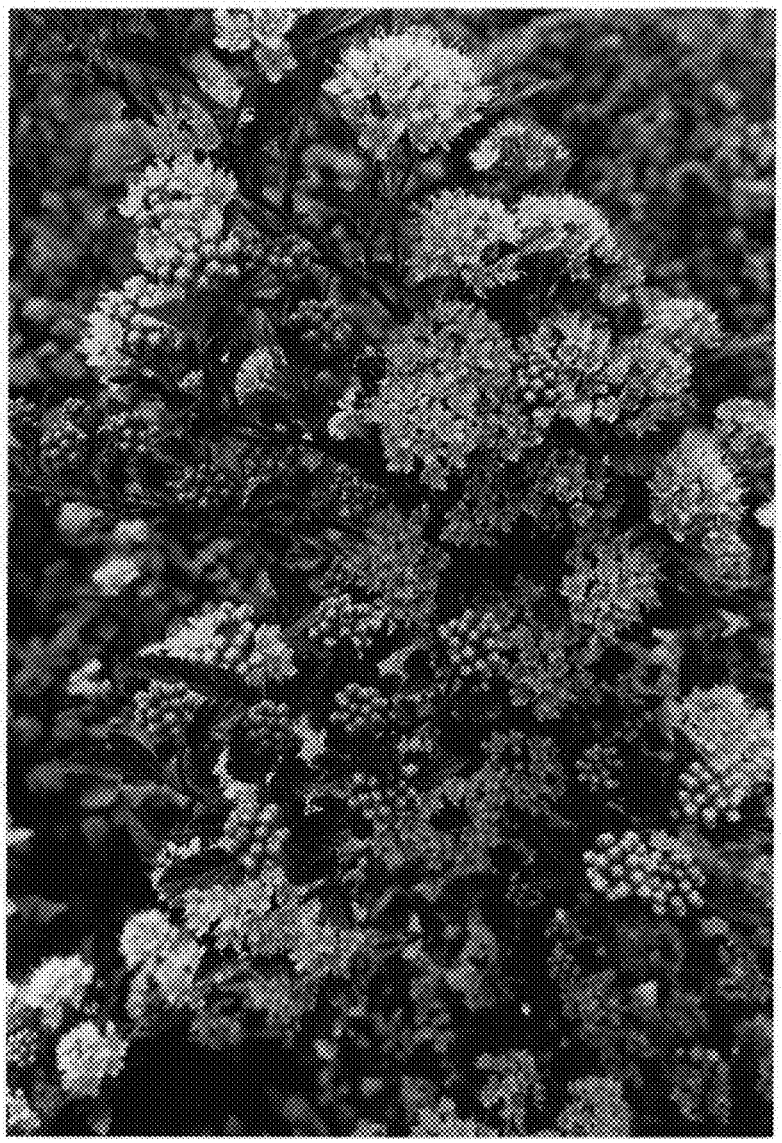
FIG. 3 illustrates corymbs of flowers at different stages of opening of 'ZLEBic5' in mid-June 2016.
Figure 4:
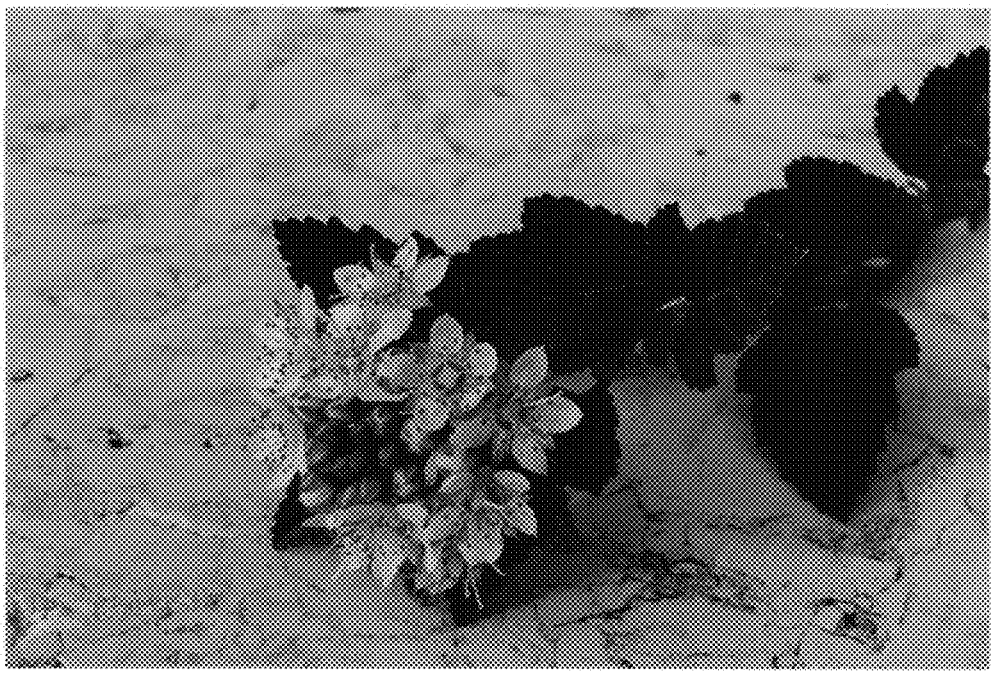
FIG. 4 illustrates a close-up view of one corymb of flowers of 'ZLEBic5' mid-June 2017.
Figure 5:
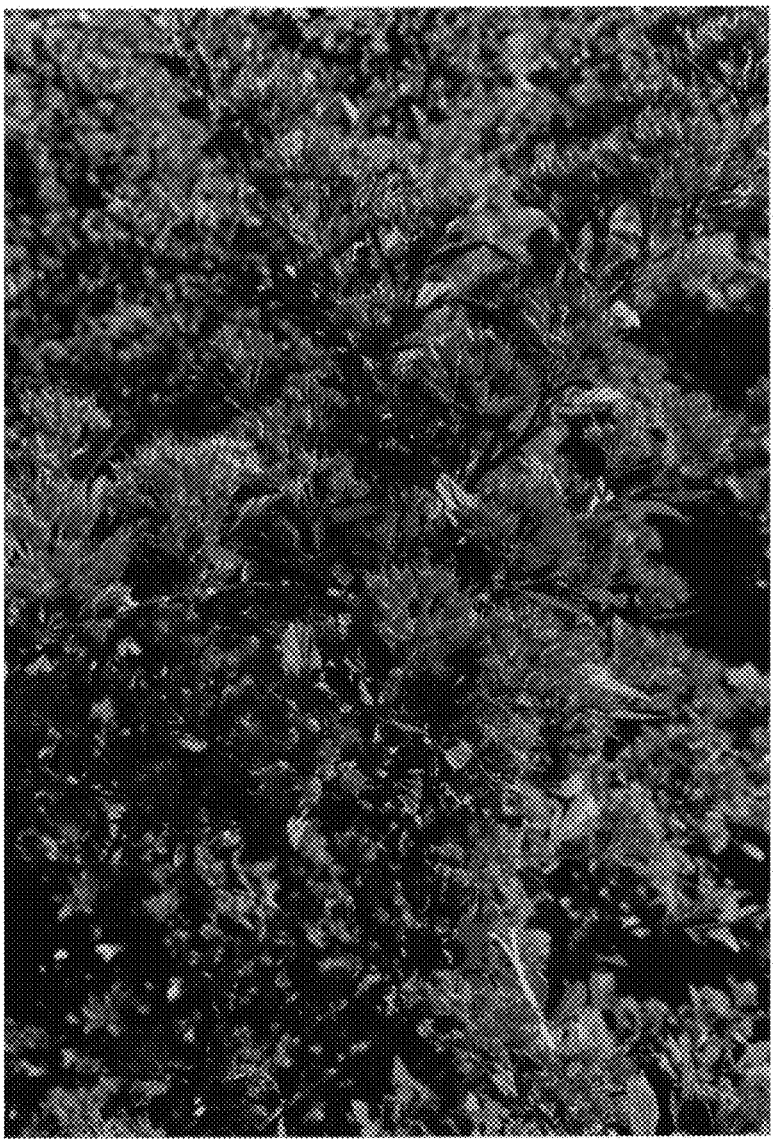
FIG. 5 illustrates developing follicles of 'ZLEBic5' in July 2016.
Figure 6:
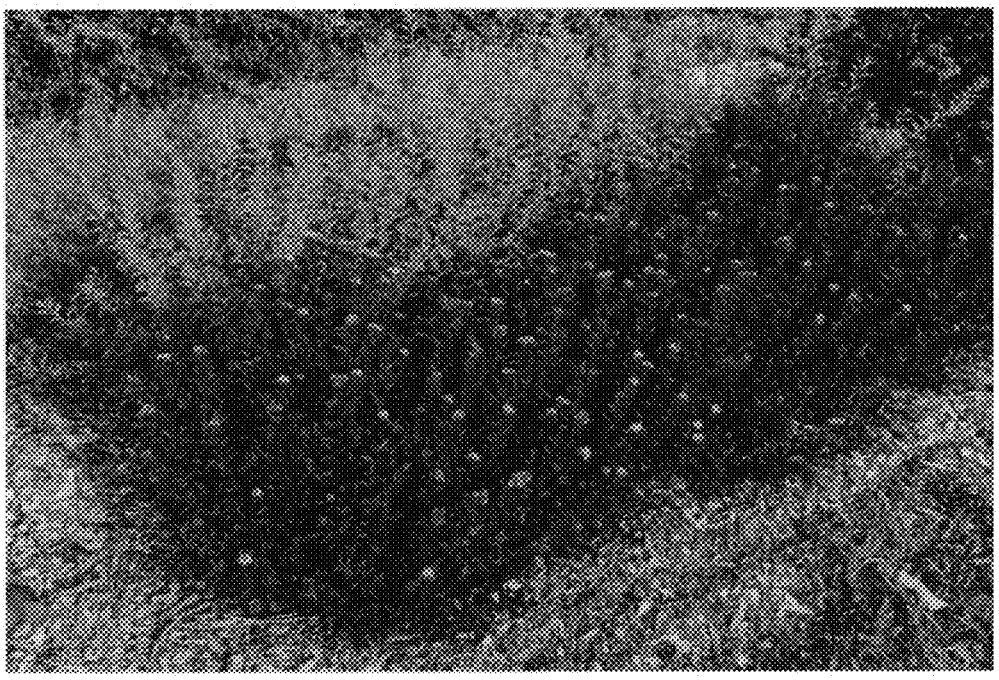
FIG. 6 illustrates abundant flowering and natural branching on a hedgerow of four closely planted two-year-old plants of 'ZLEBic5' mid-September 2017.
Figure 7:
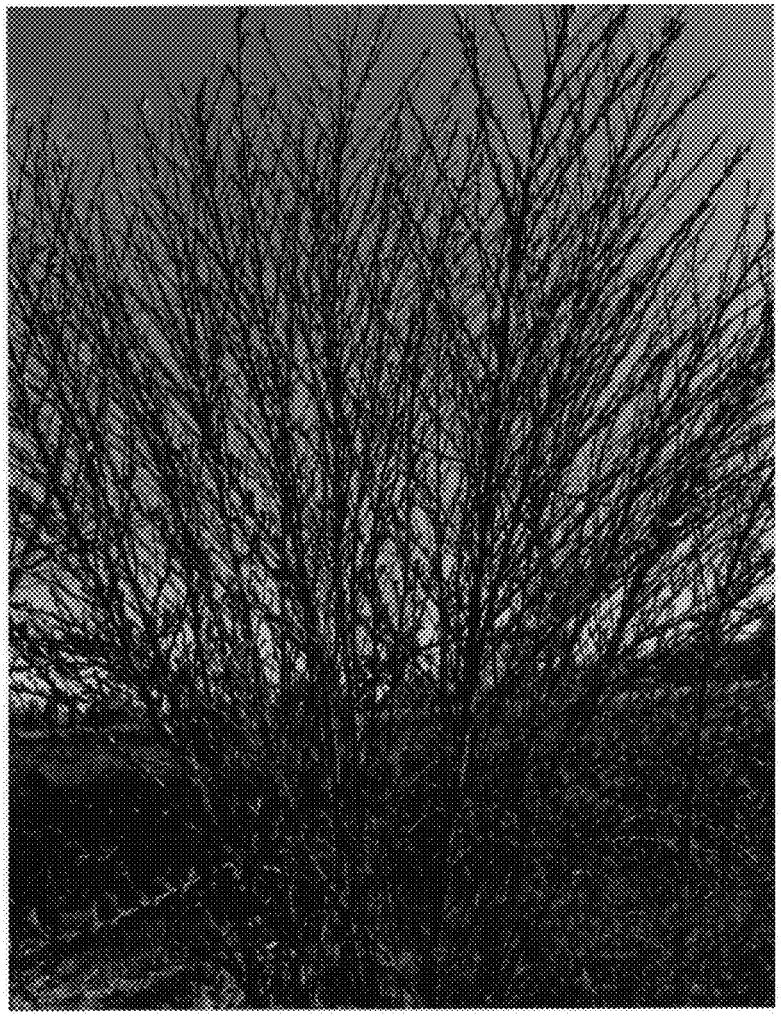
FIG. 7 illustrates the strong branching habit of an unpruned plant of 'ZLEBic5' as buds begin to swell April 2017.

The following is a detailed description of 'ZLEBic5', the new *Physocarpus opulifolius* cultivar, with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of the original seedling during its fifth year of growth in 2016 in River Falls, Wis. and two and three-year-old plants propagated from semi-hardwood cuttings.

Classification:

*Botanical.*—*Physocarpus opulifolius* 'ZLEBic5'.

*Common name of species.*—*Physocarpus* or ninebark.

*Commercial.*—Deciduous shrub.

Parentage:

*Seed parent.*—*Physocarpus opulifolius* 'Donna May' (disclosed in U.S. Plant Pat. No. 22,634).

*Pollen parent.*—*Physocarpus opulifolius* 'Dart's Gold' (not patented).

General description:

*Plant habit.*—Upright, mounded, and compact.

*Plant size.*—1.0-1.2 m in overall height and width.

*Growth habit.*—Vigorous and dense with abundant branching.

*Blooming period.*—About 21 days from mid-June to early July. Plants rebloom on terminals of new growth typically from August into October.

*Hardiness.*—Cold hardy to USDA Zone 3.

*Root description.*—Fibrous and vigorous.

*Diseases and pest resistance.*—Powdery mildew has not been observed on 'ZLEBic5', even with other ninebark genotypes infected with powdery mildew growing adjacent to 'ZLEBic5'. There are multiple species of fungi that cause powdery mildew on ninebark, and it was unclear which species of fungi were infecting the adjacent, susceptible ninebark genotypes. No other diseases or insect pests of ninebark have been observed on 'ZLEBic5'.

*Cultural requirements*.—'ZLEBic5' does well in full to partial sun and well-drained, moderately fertile soil.

Growth and propagation:

*Propagation*.—Softwood and semi-hardwood stem cuttings have been effective.

*Time required for root initiation and initial development*.—It takes about 3 to 4 weeks during the summer using intermittent mist in the greenhouse without supplemental lighting for cuttings to typically form visible roots.

*Time required to obtain a well-rooted cutting*.—It takes about 6 to 7 weeks to produce a well-rooted cutting in a 2 inch container.

Branch description:

*Branch color*.—The color of current season stems is Greyed-Red Group 178A. The most mature stems on a five-year-old plant had a mixture of colors on the exfoliating bark; primarily Greyed-Orange Group 165C, but there were also areas of Greyed-Orange Group 165A, Greyed-Orange Group 165B, Greyed-Orange Group 165D, and Orange-White Group 159B.

*Branch size*.—Branches produced during the current season of growth ranged from approximately 15 cm to 60 cm in length and 1 to 4 mm in width. The oldest branches on a five-year plant were up to 2.0 cm in diameter at the base of the plant.

*Branch surface*.—Young stems: Glabrous with a slight sheen. Older stems: Exfoliating bark layers that are somewhat dull and no longer have a sheen.

*Internode length*.—1.0 to 2.0 cm.

*Branch habit*.—Well-branched with the potential for lateral branches at most any node. Branching from axillary buds on strong current season's stems is common without the terminal being pruned out into early summer. Most vigorously growing stems by mid to late summer (August and September) terminate in a second flush of flowers and this stimulates more current season axillary buds to grow and contributes to additional branching. The angle between the new stems arising from axillary buds and the stem from which they originated is typically 15-60°.

Foliage description:

*Overall leaf size*.—Overall leaf length is up to about 4.0 cm (average 3.75 cm) and 1.75-2.0 cm wide.

*Leaf division*.—Simple.

*Leaf attachment*.—Petiolate.

*Leaf arrangement*.—Alternate.

*Leaf number*.—It varies, but an actively growing branch can easily produce 30-60 leaves in a growing season.

*Leaf blade shape*.—Ovate in overall leaf blade outline with three prominent lobes.

*Leaf blade base*.—Rounded to slightly cordate.

*Leaf blade apex*.—Acute.

*Leaf blade venation*.—Primary venation is palmate with three principal veins. Each principal vein diverges at the juncture of the leaf blade and petiole and travels through the middle of one of the three lobes. Secondary venation off of the three principal veins is pinnate.

*Leaf blade margin*.—The three primarily lobes have secondary undulations or lobes. The margin on the three primary lobes is best described then as doubly serrate.

*Leaf blade surface*.—Glabrous on upper and lower surfaces.

*Leaf blade size*.—The leaf blade is approximately 2.5-3.0 cm long and 1.75-2.0 cm wide.

*Leaf blade color*.—Young emerging leaf blades are Greyed-Orange Group 176A on the upper and lower surfaces. Young recently expanded leaf blades are closest to Greyed-Purple Group 187A on the upper surface and most of the lower surface except for veins on the lower surface are Greyed-Green Group 191A. Mature leaves are Greyed-Purple Group 187A on the upper surface and Greyed-Green Group 191A throughout the lower surface. Leaf vein color does not differ from the rest of leaf blade except for only the lower surface of young recently expanded leaves as previously described.

*Petiole size*.—About 0.75-1.25 cm in length and about 1 mm in width.

*Petiole shape*.—Sulcate. The petiole is generally round except for a longitudinal furrow running the length of the upper surface.

*Petiole color*.—Greyed-Purple Group 183C.

*Petiole texture*.—Glabrous.

*Stipule number*.—There are two stipules at each node with one on each side of the leaf petiole where it attaches to the stem.

*Stipule size*.—2-3 mm long and 1.25 mm wide.

*Stipule shape*.—Generally lanceolate.

*Stipule color*.—Greyed-Purple Group 183A.

Flower description:

*Inflorescence type*.—A corymb with 15-24 rotate flowers arranged in a hemisphere.

*Inflorescence size*.—Typically 1.5-2.0 cm in height and width.

*Inflorescence lastingness*.—The corymb has open flowers typically for up to 21 days with each individual flower open for approximately 3 days.

*Flower bud shape*.—Elliptic.

*Flower bud size and proportions*.—2.5-3.0 mm in length and 2.5-3.0 mm in width. The receptacle of the bud accounts for about half of the proximal end and the calyx accounts for about half of the distal end of an unopened flower bud.

*Flower bud color*.—The overall color of the unopened buds can best be described as Orange-Red Group N34C. This color is the result of a green base color overlaid with red.

*Flower size when fully open*.—4.0-5.0 mm in diameter and 4.0 mm in depth (not including pedicel).

*Flower fragrance*.—Slight and sweet.

*Petal number*.—5.

*Petal size*.—2.5-3.0 mm in length and width.

*Petal shape*.—Elliptic to obovate.

*Petal color*.—Just as the flowers open, the lower petal surface just as the sepals separate is a light pink and is Red-Purple Group 62D. Expanding petals are White Group N155B on the upper surface and White Group N155C on the lower surface. Fully expanded petals are White Group N155B on both the upper and lower surfaces. Aging petals can develop a soft pink color close to Red Group 49D right before petal drop.

*Sepal number.*—5.

*Sepal size.*—Length is 3.0 mm and width is 1.5-2.0 mm.

*Sepal shape.*—Deltoid.

*Sepal color.*—Orange-Red Group N34C.

*Pedicel size.*—The length ranges from about 1.5 cm for the flowers around the perimeter of the corymb to about 0.7 cm for the flowers nearest the terminal or center of the corymb. All pedicels are about 1.0 mm in diameter.

*Pedicel color.*—Orange Red Group N34C. This color is the result of a green base color overlaid with red.

*Subtending bract size.*—There is a subtending bract where each peduncle meets the central stem of the corymb. The subtending bract is 2.0-3.0 mm long and 1 mm wide below the peduncles at the proximal end of the corymb to 1.0-1.25 mm long and 0.75-1.0 mm wide for the more distal peduncles at the terminal of the corymb.

*Subtending bract shape.*—Elliptic to obovate.

*Subtending bract color.*—Orange-Red Group N34A.

Gynoecium:

*Pistil number per flower.*—Typically there are 4, but sometimes 3.

*Stigma shape.*—Globular.

*Stigma size.*—0.25 mm in diameter.

*Stigma color.*—Yellow Green Group 146D.

*Style shape.*—Linear.

*Style size.*—About 4 mm long and 0.2 mm wide.

*Style color.*—Yellow Group 145D.

*Ovary shape.*—Elliptic.

*Ovary size.*—About 0.3 mm in height and 0.25 mm in width.

*Ovary color.*—Yellow Green Group 145C with Red Purple Group 73B highlights, especially when exposed to direct sunlight.

Androecium:

*Stamen number per flower.*—Approximately 25.

*Anther shape.*—Elliptic to round.

*Anther size.*—About 0.5 mm in height and width.

*Anther color.*—Red Group 53A.

*Pollen color.*—White Group 155C.

*Pollen abundance.*—Moderate.

*Filament shape.*—Linear.

*Filament size.*—1.0-3.0 mm long and 0.1-0.2 mm wide.

*Filament color.*—Yellow Group 145D.

Fruit and seeds:

*Fruit.*—There are typically three or four firm-walled follicles that form per flower. Follicles split along both sides of the seam, but split more readily along the inner or adaxial seam. Follicles are elongated and generally ovate in shape with acuminate tips. They are up to 6.0 mm long and approximately 2.0 mm wide and range in color from Greyed-Purple Group 183A to Greyed-Green Group 193A. Follicle color tends to be green when out of direct sunlight and increasingly purple the more direct sunlight that is received. Once mature, follicles dry and turn Greyed-Orange Group 165A.

*Seeds per follicle.*—There are up to 2 seeds per follicle.

*Seed shape.*—Ovate.

*Seed size.*—Generally 1.5 mm long and 1.25 mm wide.

*Seed color.*—Mature seed color is between Greyed-Orange Group 164D and Greyed-Orange Group 165D.

Cytology:

*Ploidy.*—Diploid (2n=2x=18). Meristematic root tip cells in the stage of metaphase of mitosis were observed to have 18 chromosomes under a compound microscope at 400× magnification.

Winter hardiness: Acclimated plants of 'ZLEBic5' have displayed strong stem survival (complete survival to minor tip dieback) in United States Department of Agriculture cold hardiness zone 3 and warmer without insulation.

I claim:

1. A new and distinct cultivar of *Physocarpus opulifolius* plant substantially as herein shown and described, characterized particularly by an upright, mounded, dense plant habit; compact overall plant size; strong branching characteristics; small orange-red foliage as it emerges that matures to purple; short internode length; resistance to powdery mildew; corymbs of small pink-white flowers that are produced in late spring into early summer and again on current season terminal growth later in summer and into fall; coral pink to red follicle color in full sun for about a month after fertilization; and ability to root and grow vigorously from softwood and semi-hardwood stem cuttings.

* * * * *